US00PP19933P2

(12) United States Plant Patent
Sakazaki

(10) Patent No.: US PP19,933 P2
(45) Date of Patent: Apr. 21, 2009

(54) ***SCOPARIA* PLANT NAMED 'USSCO401-3'**

(50) Latin Name: *Scoparia hybrid*
Varietal Denomination: USSCO401-3

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 12/070,564

(22) Filed: Feb. 19, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Annette H Para
*Assistant Examiner*—S B McCormick Ewoldt
(74) *Attorney, Agent, or Firm*—C. A. Whealy

(57) ABSTRACT

A new and distinct cultivar of *Scoparia* plant named 'USSCO401-3', characterized by its low-mounding and outwardly spreading growth habit; freely branching habit; early and freely flowering habit; small yellow-colored flowers; and good garden performance.

1 Drawing Sheet

Botanical designation: *Scoparia* hybrid.
Cultivar denomination: 'USSCO401-3'.

BACKGROUND OF THE INVENTION

The present invention relates to a new and distinct cultivar of *Scoparia,* botanically known as *Scoparia* hybrid and hereinafter referred to by the name 'USSCO401-3'.

The new *Scoparia* is a product of a planned breeding program conducted by the Inventor in Hikone, Shiga, Japan. The objective of the breeding program is to create new *Scoparia* cultivars with uniform plant habit and numerous attractive flowers.

The new *Scoparia* originated from a cross-pollination made by the Inventor on Apr. 10, 2004 in Hikone, Shiga, Japan of an unnamed selection of *Scoparia montevidensis,* not patented, as the female, or seed, parent with the *Scoparia* hybrid cultivar Suntutuki, disclosed in U.S. Plant Pat. No. 16,345, as the male, or pollen, parent. The new *Scoparia* was discovered and selected by the Inventor as a single flowering plant within the progeny of the stated cross-pollination in a controlled environment in Bonsall, Calif. on May 26, 2005.

Asexual reproduction of the new *Scoparia* by terminal cuttings in a controlled environment in Bonsall, Calif. since Jul. 1, 2005 has shown that the unique features of this new *Scoparia* are stable and reproduced true to type in successive generations.

SUMMARY OF THE INVENTION

The cultivar USSCO401-3 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'USSCO401-3'. These characteristics in combination distinguish 'USSCO401-3' as a new and distinct cultivar of *Scoparia:*

1. Low-mounding and outwardly spreading growth habit.
2. Freely branching habit.
3. Early and freely flowering habit.
4. Small yellow-colored flowers.
5. Good garden performance.

The new *Scoparia* can be compared to plants of the female parent selection. Plants of the new *Scoparia* differ from plants of the female parent selection in the following characteristics:

1. Plants of the new *Scoparia* are more vigorous than plants of the female parent selection.
2. Plants of the new *Scoparia* and the female parent selection differ in leaf shape as plants of the female parent selection have rounded leaves.

Plants of the new *Scoparia* can be compared to plants of the male parent, the cultivar Suntutuki. Plants of the new *Scoparia* differ from plants of the cultivar Suntutuki in the following characteristics:

1. Plants of the new *Scoparia* are more vigorous than plants of the cultivar Suntutuki.
2. Plants of the new *Scoparia* flower earlier than plants of the cultivar Suntutuki.
3. Leaves of plants of the new *Scoparia* are not as lacy as leaves of plants of the cultivar Suntutuki.

Plants of the new *Scoparia* can be compared to plants of the cultivar Melongolly Blue, not patented. In side-by-side comparisons conducted in Bonsall, Calif., plants of the new *Scoparia* differed from plants of the cultivar Melongolly Blue in the following characteristics:

1. Plants of the new *Scoparia* were not as upright as plants of the cultivar Melongolly Blue.
2. Plants of the new *Scoparia* and the cultivar Melongolly Blue differed in flower color as plants of the cultivar Melongolly Blue had blue-colored flowers.

BRIEF DESCRIPTION OF THE PHOTOGRAPHS

The accompanying colored photographs illustrate the overall appearance of the new *Scoparia,* showing the colors as true as it is reasonably possible to obtain in colored reproductions of this type. Colors in the photographs may differ slightly from the color values cited in the detailed botanical description which accurately describe the colors of the new *Scoparia*.

The photograph at the bottom of the sheet comprises a side perspective view of a typical flowering plant of 'USSCO401-3' grown in a container.

The photograph at the top of the sheet comprises a close-up of typical flowers and leaves of 'USSCO401-3'.

DETAILED BOTANICAL DESCRIPTION

The aforementioned photographs and following observations, measurements and values describe plants grown in Bonsall, Calif., under commercial practice during the late summer and early autumn in a polyethylene-covered greenhouse with day temperatures ranging from 16° C. to 38° C. and night temperatures ranging from 13° C. to 24° C. Rooted young plants were grown for about eleven weeks in one-gallon containers. In the following description, color references are made to The Royal Horticultural Society Colour Chart, 1995 Edition, except where general terms of ordinary dictionary significance are used.

Botanical classification: *Scoparia* hybrid cultivar USSCO401-3.

Parentage:

*Female, or seed, parent.*—Unnamed selection of *Scoparia montevidensis,* not patented.

*Male, or pollen, parent.*—*Scoparia* hybrid cultivar Suntutuki, disclosed in U.S. Plant Pat. No. 16,345.

Propagation:

*Type.*—By vegetative cuttings.

*Time to produce a rooted young plant.*—About two to three weeks.

*Root description.*—Fine; white in color.

*Rooting habit.*—Freely branching; moderately dense.

Plant description:

*Plant and growth habit.*—Low-mounding and outwardly spreading growth habit. Freely basal branching habit with about ten basal branches each basal branch with about 20 secondary branches. Vigorous growth habit.

*Plant height.*—About 17 cm.

*Plant diameter.*—About 34 cm by 39 cm.

Lateral branch description:

*Length.*—About 21 cm.

*Diameter.*—About 1 mm.

*Internode length.*—About 1 cm.

*Strength.*—Slender, wiry, moderately strong.

*Aspect.*—Initially upright to outwardly spreading to decumbent.

*Texture.*—Smooth, glabrous.

*Color.*—144A.

Foliage description:

*Arrangement.*—Opposite becoming whorled at the apices; simple.

*Length.*—About 6 mm.

*Width.*—About 3 mm.

*Shape.*—Roughly lanceolate and somewhat lacy in appearance; tridentate to five-lobed.

*Apex.*—Acute.

*Base.*—Attenuate.

*Margin.*—Laciniate.

*Texture, upper and lower surfaces.*—Smooth, glabrous.

*Venation pattern.*—Pinnate.

*Color.*—Developing foliage, upper surface: 146A. Developing foliage, lower surface: 147B. Fully expanded foliage, upper and lower surfaces: 146B; venation, 146B.

*Petiole.*—Length: About 9 mm. Diameter: About 1 mm. Texture, upper and lower surfaces: Smooth, glabrous. Color, upper and lower surfaces: 146B.

Flower description:

*Flower arrangement and habit.*—Single star-shaped flowers arranged in axillary clusters of three or four. Freely flowering habit with usually about 75 to 85 open flowers and flower buds per lateral branch. Flowers persistent. Flowers face mostly outwardly.

*Fragrance.*—None detected.

*Natural flowering season.*—Plants of the new *Scoparia* initiate and develop flowers about five weeks after planting. Plants flower continuously from June to September in Southern California.

*Flower longevity.*—Individual flowers last about five to six days on the plant.

*Flower diameter.*—About 1.1 cm.

*Flower length (height).*—About 6 mm.

*Flower bud.*—Shape: Ovoid. Length: About 4 mm. Diameter: About 2.5 mm. Color: 4A.

*Petals.*—Arrangement: Four petals in a single whorl. At the base of the petals and subtending the stamens is an upright corona of about 100 hairs, which are about 3 mm in length and 1A in color. Length: About 5 mm. Width: About 4 mm. Shape: Elliptical. Apex: Acute. Base: Truncate. Margin: Entire. Texture, upper and lower surfaces: Smooth, glabrous. Color: When opening and fully opened, upper surface: 8A. When opening and fully opened, lower surface: 8B.

*Sepals.*—Arrangement: Five in a single whorl. Length: About 3 mm. Width: About 1 mm. Shape: Elliptical to lanceolate. Apex: Acute. Base: Truncate. Margin: Entire. Texture, upper and lower surfaces: Smooth, glabrous. Color, upper and lower surfaces: 146C.

*Peduncles.*—Length: About 1.2 cm. Diameter: Less than 1 mm. Angle: About 30° to 45° from stem axis. Strength: Moderately strong; wiry. Texture: Smooth, glabrous. Color: 144B.

*Reproductive organs.*—Stamens: Quantity: About four per flower. Filament length: About 2 mm. Filament color: 1A. Anther shape: Oblong. Anther length: About 1.5 mm. Anther color: 8B. Pollen amount: Sparse. Pollen color: 8D. Pistils: Quantity: One per flower. Pistil length: About 4 mm. Style length: About 1.5 cm. Style color: 145B. Stigma shape: Rounded. Stigma color: 145A. Ovary color: 145A.

*Seed/fruit.*—Seed and fruit development have not been observed on plants of the new *Scoparia*.

Garden performance: Plants of the new *Scoparia* have been observed to have good garden performance and tolerate wind, rain and temperatures ranging from about 10° C. to about 40° C.

Pathogen/pest resistance: Plants of the new *Scoparia* have not been observed to be resistant to pathogens and pests common to *Scoparia*.

It is claimed:

1. A new and distinct *Scoparia* plant named 'USSCO401-3' as illustrated and described.

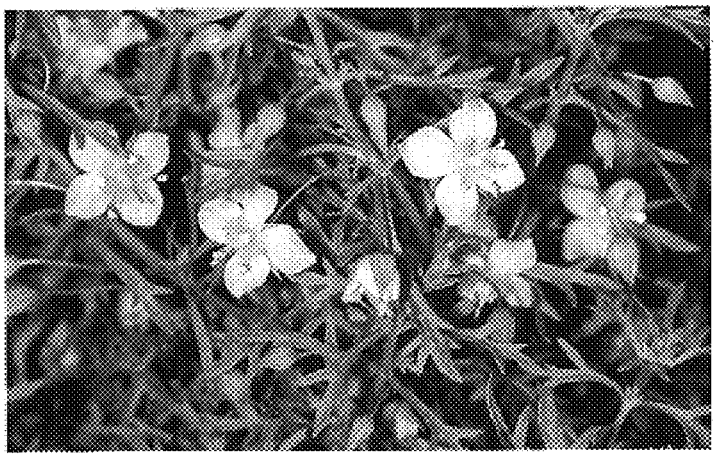
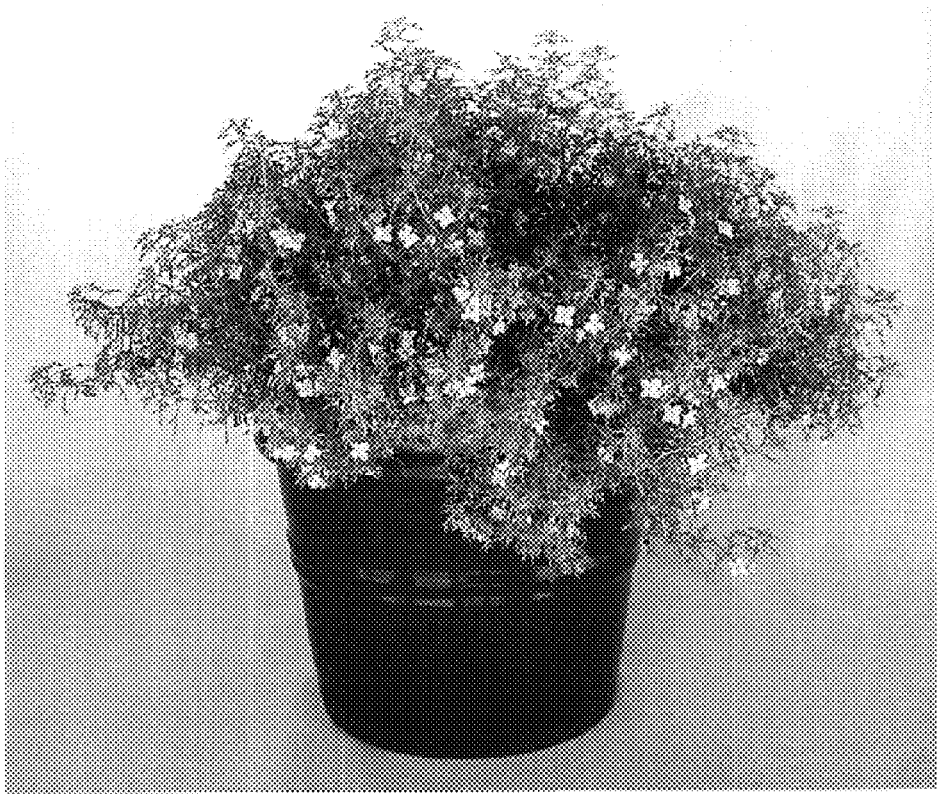

* * * * *